United States Patent [19]
Wachter et al.

[11] Patent Number: 6,045,785
[45] Date of Patent: Apr. 4, 2000

[54] DEODORIZING PREPARATIONS

[75] Inventors: Rolf Wachter, Duesseldorf; Holger Tesmann, Juechen; Ansgar Behler, Bottrop; Karl-Heinz Maurer, Erkrath, all of Germany

[73] Assignee: Henkel Kommanditgesellschaft auf Aktien, Duesseldorf, Germany

[21] Appl. No.: 09/284,666

[22] PCT Filed: Oct. 8, 1997

[86] PCT No.: PCT/EP97/05523

§ 371 Date: Apr. 16, 1999

§ 102(e) Date: Apr. 16, 1999

[87] PCT Pub. No.: WO98/17241

PCT Pub. Date: Apr. 30, 1998

[30] Foreign Application Priority Data

Oct. 17, 1996 [DE] Germany .................. 196 42 874

[51] Int. Cl.$^7$ .................. A61K 7/32; A61K 7/38; A61K 7/00
[52] U.S. Cl. .................. 424/65; 424/68; 424/400; 424/401
[58] Field of Search .................. 424/65, 68, 401, 424/400

[56] References Cited

U.S. PATENT DOCUMENTS 4,450,151  5/1984  Shinozawa .................. 424/47

*Primary Examiner*—Shelley A. Dodson
*Attorney, Agent, or Firm*—John E. Drach; Glenn E. J. Murphy

[57] ABSTRACT

The invention relates to novel deodorizing preparations with increased synergetic performance containing (a) sterol sulfate, (b1) aluminum chlorhydrate, (b2) esterase inhibitors and/or (b3) bactericidal or bacteriostatic active substances.

14 Claims, No Drawings

DEODORIZING PREPARATIONS

FIELD OF THE INVENTION

This invention relates to deodorizing formulations containing sterol sulfates, aluminium chlorohydrate, esterase inhibitors and bactericidal/bacteriostatic agents and to the use of sterol sulfates for the production of cosmetic formulations, for example deodorizing formulations.

DISCUSSION OF THE RELATED ART

In the field of personal hygiene, deodorants are used to eliminate troublesome body odors. Body odors are formed by the bacterial decomposition of basically odorless perspiration, particularly in the damp underarm regions or under similar conditions favorable to microorganism growth. Body odors can be masked by suitable perfumes. They can also be controlled by using formulations which inhibit the actual secretion of perspiration or its decomposition (so-called antihydrotics, antiperspirants or antitranspirants). Typical examples of such substances are aluminium compounds, such as aluminium sulfate or aluminium chlorohydrate, zinc salts and citric acid compounds. An overview of these agents was published, for example, in Umbach (Ed.), "Kosmetik", pages 141 et seq., Thieme Verlag, Stuttgart, 1988.

However, it is clear from everyday living that the problem of odor inhibition, particularly in heat or in the event of bodily activity, has by no means been completely solved. Commercial products are unable permanently to suppress the secretion of perspiration or the formation of odors. Instead, their inhibiting effect is of limited duration and is also dependent on the extent to which perspiration is secreted. Accordingly, there is a constant need for improved products which minimize the secretion of perspiration and reduce the formation of body odors and which, at the same time, show increased dermatological compatibility, i.e. reduced irritation potential towards particularly sensitive skin. The problem addressed by the present invention was to provide such products.

DESCRIPTION OF THE INVENTION

The present invention relates to deodorizing formulations containing (a) sterol sulfates,
(b1) aluminium chlorohydrate,
(b2) esterase inhibitors and/or
(b3) bactericidal or bacteriostatic agents.

The use of aluminium chlorohydrates, esterase inhibitors (for example triethyl citrate) and bactericidal agents (for example chitosan) for the production of deodorizing and/or perspiration-inhibiting compositions is known from the prior art. It has surprisingly been found that sterol sulfates inhibit the activity of esterolytic enzymes, even in the lower ppm range, and that a synergistic deodorizing effect is obtained together with the components mentioned above. These sterol sulfates act selectively on serine esterases and serine proteases without impairing the biological equilibrium of the skin flora. At the same time, the use of sterol sulfates leads to an improvement in the skin-cosmetic compatibility of the products.

Sterol Sulfates

Sterol sulfates are known substances which may be prepared, for example, by sulfation of sterols with a complex of sulfur trioxide and pyridine in benzene [cf. J. Am. Chem. Soc. 63, 1259 (1941)]. Sterols—which may be used as starting materials for the production of sterol sulfates—are understood to be steroids which contain only a hydroxyl group at C-3 but no other functional groups. Formally, therefore, they are alcohols which would explain why this group of compounds is sometimes also referred to as sterols. Generally, sterols contain 27 to 30 carbon atoms and one double bond in the 5/6 position and optionally in the 7/8, 8/9 or other positions. Besides these unsaturated species, however, other suitable starting materials are the saturated compounds obtainable by hydrogenation. Typical examples of suitable sterol sulfates are those based on zoosterols, for example animal cholesterol, lanosterols from wool fat, spongosterols from sponges or stellasterols from starfish. However, phytosterol sulfates, for example those based on ergosterols, campesterols, stigmasterols and sitosterols, are preferably used by virtue of the lighter color of the sulfation products.

Aluminium Chlorohydrate

The aluminium chlorohydrates of component (b1) are colorless hygroscopic crystals which readily coalesce in air and which accumulate during the concentration of aqueous aluminium chloride solutions by evaporation. Aluminium chlorohydrate is used for the production of antiperspirant and deodorizing formulations and probably acts by contracting or blocking the sweat glands by protein precipitation and/or removal of moisture [cf. J. Soc. Cosm. Chem. 24, 281 (1973)]. An aluminium chlorohydrate which corresponds to the formula $[Al_2(OH)_5Cl].2.5H_2O$ is commercially available under the name of Locron® from Hoechst AG of Frankfurt, FRG. This aluminium chlorohydrate is particularly preferred for the purposes of the invention [cf. J. Pharm. Pharmacol. 26, 531 (1975)].

Esterase Inhibitors

When perspiration is present in and around the underarm region, extracellular enzymes—esterases, preferably proteases and/or lipases—which cleave esters and thus emit odor-forming substances are activated by bacteria. The esterase inhibitors of component (c), preferably trialkyl citrates, such as trimethyl citrate, tripropyl citrate, tributyl citrate and, in particular, triethyl citrate (Hydagen® CAT, Henkel KGaA, Düsseldorf, FRG), inhibit the enzyme activity and thus reduce odor formation. The free acid is probably released by the cleavage of the citric acid ester, reducing the pH value on the skin to such an extent that the enzymes are inactivated by acylation. Other substances suitable for use as esterase inhibitors are dicarboxylic acids and esters thereof such as, for example, glutaric acid, glutaric acid monoethyl ester, glutaric acid diethyl ester, adipic acid, adipic monoethyl ester, adipic acid diethyl ester, malonic acid and malonic acid diethyl ester, hydroxycarboxylic acids and esters thereof such as, for example, citric acid, malic acid, tartaric acid or tartaric acid diethyl ester.

Bactericides or Bacteriostatic Agents

Typical examples of suitable bactericidal or bacteriostatic agents (component (b3)) are, in particular, chitosan and phenoxyethanol. 5-Chloro-2-(2,4-dichlorophenoxy)-phenol, which is marketed by Ciba-Geigy of Basel, Switzerland under the name of Irgasan®, has also proved to be particularly effective.

COMMERCIAL APPLICATIONS

Sterol sulfates have proved to be enzyme-inhibiting for the described application. Accordingly, the present invention relates to their use—either on their own or in the form of mixtures with aluminium chlorohydrates, other esterase inhibitors and/or bactericidal or bacteriostatic agents—for the production of deodorizing formulations.

In one preferred embodiment of the invention, components (a) and (b) may advantageously be used in the following quantities, based on the solids content:

(a) 0.01 to 50, preferably 0.1 to 5% by weight of sterol sulfates, (b) 1.0 to 50, preferably 10 to 50% by weight of aluminium chlorohydrate,
(c) 0.01 to 20, preferably 1 to 5% by weight of esterase inhibitors and
(d) 0.01 to 5, preferably 0.1 to 1% by weight of bactericidal or bacteriostatic agents,
with the proviso that the quantities shown add up to 100% by weight. The figures apply to the active substance content of the components.

Germ Inhibitors

The formulations according to the invention may contain known germ inhibitors as further additives. Typical examples of germ inhibitors are preservatives which act specifically against gram-positive bacteria such as, for example, 2,4,4'-trichloro-2'-hydroxydiphenyl ether, chlorhexidine (1,6-di-(4-chlorophenylbiguanido)-hexane) or TCC (3,4,4'-trichlorocarbanilide). Numerous perfumes and essential oils also have antimicrobial properties. Typical examples are the active substances eugenol, menthol and thymol in nettle, mint and thyme oil. An interesting natural deodorant is the terpene alcohol farnesol (3,7,11-trimethyl-2,6,10-dodecatrien-1-ol) which is present in linden blossom oil and which smells of lily-of-the-valley. Glycerol monolaurate has also been successfully used as a bacteriostatic agent. The percentage content of the additional germ-inhibiting agents is normally about 0.1 to 2% by weight, based on the solids component of the formulations.

Auxiliaries and Additives

To enable the active substances to be applied to the skin in a measurable, economic, convenient and cosmetically attractive manner, they are normally incorporated in formulation bases. The most important of these include alcoholic and aqueous/alcoholic solutions, emulsions, gels, oils, wax/fat compounds, stick preparations and powders. Thus, the formulations according to the invention may contain, for example, up to 60% by weight of lower aliphatic alcohols, preferably ethanol, and organic acids, for example glycolic acid. Other ingredients include superfatting agents, emulsifiers, antioxidants, talcum, silica (for example as a support for the aluminium chlorohydrate), perfume oils, essential oils, dyes and—for spray applications—propellent gases such as, for example, propane and/or butane. The formulations are preferably marketed as rollers (roll-on emulsions), sticks, deodorant or pump sprays.

EXAMPLES

The effectiveness of the formulations according to the invention was representatively determined through their inhibition of esterase. To this end, the residual activity of the test mixtures after acting on esterase for 15 minutes in concentrations of 2,000 ppm at pH 6 was determined parallel to a non-inhibited esterase (standard=100%). Compositions 1 to 6 correspond to the invention, compositions C1 to C3 are intended for comparison. The results are summarized in Table 1 (quantities in % by weight).

TABLE 1

Formulations and esterase inhibition

| Components | 1 | 2 | 3 | 4 | 5 | 6 | C1 | C2 | C3 |
|---|---|---|---|---|---|---|---|---|---|
| Sterol sulfate, sodium salt | 4 | 4 | 4 | 4 | 4 | 4 | — | — | — |
| Aluminium Chlorohydrate | — | 50 | — | 50 | 10 | 50 | 50 | — | 50 |
| Triethyl citrate | — | — | 5 | 6 | 5 | 3 | — | 5 | 5 |
| Chitosan | — | — | — | — | — | 3 | — | — | — |
| Ethanol | 20 | — | 20 | 20 | 20 | 10 | 20 | 20 | 20 |
| Glycolic acid | 0.016 | 0.016 | 0.016 | 0.016 | 0.106 | 0.016 | — | — | — |
| Farnesol | — | — | — | 1 | — | — | — | — | — |
| Water | | | | to 100 | | | | | |
| Esterase activity [%] | 78 | 73 | 75 | 30 | 28 | 27 | 100 | 77 | 75 |

We claim:

1. A deodorizing formulation comprising:
    (a) a sterol sulfate;
    (b) aluminum chlorohydrate; and
    (c) an esterase inhibitor, a bactericidal agent, or a bacteriostatic agent.

2. A formulation according to claim 1, wherein the sterol sulfate is a phytosterol sulfate.

3. A formulation according to claim 1, wherein the esterase inhibitor is a trialkyl citrate.

4. A formulation according to claim 1, wherein the bactericidal agent or the bacteriostatic agent is a chitosan.

5. A deodorizing formulation comprising:
    (a) 0.01% to 50% by weight of a sterol sulfate;
    (b) 1.0% to 50% by weight of aluminum chlorohydrate;
    (c) 0.01% to 20% by weight of an esterase inhibitor; and
    (d) 0.01% to 5% by weight of a bactericidal or bacteriostatic agent, said percents based on the total solids weight of the formulation.

6. A formulation according to claim 5, comprising:
    (a) 0.1% to 5% by weight of a sterol sulfate;
    (b) 10% to 50% by weight of aluminum chlorohydrate;
    (c) 1% to 5% by weight of an esterase inhibitor; and
    (d) 0.1% to 1% by weight of a bactericidal or bacteriostatic agent.

7. A formulation according to claim 5, wherein the sterol sulfate is derived from a sterol selected from the group consisting of phytosterols, zoosterols, lanosterols, spongosterols, and stellasterols.

8. A formulation according to claim 7, wherein the sterol sulfate is derived from a phytosterol selected from the group consisting of ergosterols, campesterols, stigmasterols, and sitosterols.

9. A formulation according to claim 5, wherein the aluminum chlorohydrate has the formula $[Al_2(OH)_5Cl] \cdot 2.5H_2O$.

10. A formulation according to claim 5, wherein the esterase inhibitor is selected from the group consisting of trialkyl citrates, dicarboxylic acids and esters thereof, and hydroxycarboxylic acids and esters thereof.

11. A formulation according to claim 10, wherein the esterase inhibitor is selected from the group consisting of trimethyl citrate, tripropyl citrate, tributyl citrate, triethyl citrate, glutaric acid, glutaric acid monoethyl ester, glutaric acid diethyl ester, adipic acid, adipic acid monoethyl ester, adipic acid diethyl ester, malonic acid, malonic acid diethyl ester, citric acid, malic acid, tartaric acid, and tartaric acid diethyl ester.

12. A formulation according to claim 5, wherein the bactericidal or bacteriostatic agent is selected from the group consisting of chitosan, phenoxyethanol, and chloro-2-(2,4-dichlorophenoxy)-phenol.

13. A deodorizing formulation comprising:
 (a) 0.01% to 50% by weight of a sterol sulfate;
 (b) 1.0% to 50% by weight of aluminum chlorohydrate; and
 (c) 0.01% to 20% by weight of an esterase inhibitor or 0.01% to 5% by weight of a bactericidal or bacteriostatic agent, said percents based on the total solids weight of the formulation, wherein the sterol sulfate is derived from a sterol selected from the group consisting of phytosterols, zoosterols, lanosterols, spongosterols, and stellasterols, the aluminum chlorohydrate has the formula $[Al_2(OH)_5Cl].2.5H_2O$, the esterase inhibitor is selected from the group consisting of trialkyl citrates, dicarboxylic acids and esters thereof, and hydroxycarboxylic acids and esters thereof, and the bactericidal or bacteriostatic agent is selected from the group consisting of chitosan, phenoxyethanol, and chloro-2-(2,4-dichlorophenoxy)-phenol.

14. A formulation according to claim 13, wherein the sterol sulfate is derived from a phytosterol selected from the group consisting of ergosterols, campesterols, stigmasterols, and sitosterols, and the esterase inhibitor is selected from the group consisting of trimethyl citrate, tripropyl citrate, tributyl citrate, triethyl citrate, glutaric acid, glutaric acid monoethyl ester, glutaric acid diethyl ester, adipic acid, adipic acid monoethyl ester, adipic acid diethyl ester, malonic acid, malonic acid diethyl ester, citric acid, malic acid, tartaric acid, and tartaric acid diethyl ester.

* * * * *